United States Patent
Cruz Duarte et al.

(10) Patent No.: US 11,642,439 B2
(45) Date of Patent: May 9, 2023

(54) INJECTABLE AND EXPANDABLE COMPOSITION, DEVICES, KITS, METHODS AND USES THEREOF

(71) Applicants: UNIVERSIDADE DO MINHO, Braga (PT); ASSOCIATION FOR THE ADVANCEMENT OF TISSUE ENGINEERING AND CELL BASED TECHNOLOGIES & THERAPIES (A4TEC)—ASSOCIACAO, Braga (PT)

(72) Inventors: Ana Rita Cruz Duarte, Charneca da Caparica (PT); Rui L. Reis, Oporto (PT); Jorge Manuel Nunes Correia Pinto, Oporto (PT); Rui Miguel Fernandes Duarte, Braga (PT)

(73) Assignees: UNIVERSIDADE DO MINHO, Braga (PT); ASSOCIATION FOR THE ADVANCEMENT OF TISSUE ENGINEERING AND CELL BASED TECHNOLOGIES & THERAPIES (A4TEC)—ASSOCIAÇÃO, Guimaraes (PT)

( * ) Notice: Subject to any disclaimer, the term of this patent is extended or adjusted under 35 U.S.C. 154(b) by 184 days.

(21) Appl. No.: 16/755,811

(22) PCT Filed: Oct. 15, 2018

(86) PCT No.: PCT/IB2018/057985
§ 371 (c)(1),
(2) Date: Apr. 13, 2020

(87) PCT Pub. No.: WO2019/073463
PCT Pub. Date: Apr. 18, 2019

(65) Prior Publication Data
US 2021/0187159 A1    Jun. 24, 2021

(30) Foreign Application Priority Data

Oct. 13, 2017  (PT) .................................. 110348
Jan. 22, 2018  (EP) .................................. 18152785

(51) Int. Cl.
*A61L 27/18* (2006.01)
*A61L 27/34* (2006.01)
(Continued)

(52) U.S. Cl.
CPC ............... *A61L 27/18* (2013.01); *A61L 27/34* (2013.01); *A61L 27/54* (2013.01); *A61M 5/2053* (2013.01);
(Continued)

(58) Field of Classification Search
None
See application file for complete search history.

(56) References Cited

U.S. PATENT DOCUMENTS 5,574,075 A    11/1996  Draenert
2010/0211058 A1    8/2010  Winterbottom et al.
(Continued)

FOREIGN PATENT DOCUMENTS

WO    20110146852    11/2011

OTHER PUBLICATIONS

A. P. Duarte et al., "Surgical adhesives: Systematic review of the main types and development forecast", Prog. Polym. Sci., Aug. 2012, pp. 1031-1050, vol. 37.
(Continued)

*Primary Examiner* — Casey S Hagopian
(74) *Attorney, Agent, or Firm* — Leason Ellis LLP

(57) ABSTRACT

The present disclosure relates to injectable and expandable compositions, devices, kits and methods for use in an approach for the in-situ foaming of polymers for bone or
(Continued)

tissue defects, namely to fill and/or fuse a tissue defect. The present disclosure relates to compositions, devices, kits and methods for use in an approach for the in-situ foaming of polymers for bone or tissue defects, namely for bone tissue defect filling/fusion. The design of extendable and expandable compositions for bone fusion is one of the most challenging fields in the intersection of polymer and biomedical engineering. An aspect of the present disclosure relates to an injectable expandable composition for use in medicine, veterinary or cosmetic, comprising a polycaprolactone particle filler; a polydopamine adhesive bound to said filler; a polymethacrylic acid plasticizer bound to said polydopamine adhesive.

14 Claims, 9 Drawing Sheets

(51) Int. Cl.
A61L 27/54 (2006.01)
A61M 5/20 (2006.01)
C08L 33/00 (2006.01)
C08L 67/04 (2006.01)
C08L 77/04 (2006.01)

(52) U.S. Cl.
CPC .............. C08L 33/00 (2013.01); C08L 67/04 (2013.01); C08L 77/04 (2013.01); A61L 2400/06 (2013.01); A61L 2400/08 (2013.01); A61L 2430/02 (2013.01); A61L 2430/38 (2013.01)

(56) References Cited

U.S. PATENT DOCUMENTS

2011/0288651 A1* 11/2011 Kannan ................ A61P 43/00
623/23.61
2017/0266123 A1* 9/2017 Amoozgar ........... A61K 9/5192

OTHER PUBLICATIONS

Bong Hoon Kim et al., "Mussel-Inspired Block Copolymer Lithography for Low Surface Energy Materials of Teflon, Graphene, and Gold," Advanced Materials, Dec. 2011, pp. 5618-5622, vol. 23.
D. F. Farrar, "Bone adhesives for trauma surgery: A review of challenges and developments", Int. J. Adhes. Adhes., Mar. 2012, pp. 89-97, vol. 33.
D. J. Mooney, et al., "Novel approach to fabricate porous sponges of poly(D,L-lactic-co-glycolic acid) without the use of organic solvents," Biomaterials, Jul. 1996, pp. 1417-1422, vol. 17.
D. Zhang et al., "A bioactive "self-fitting" shape memory polymer scaffold with potential to treat cranio-maxillo facial bone defects", Acta Biomaterialia, Nov. 2014, pp. 4597-4605.
H. Lee et al., "Mussel-Inspired Surface Chemistry for Multifunctional Coatings," SCIENCE, Oct. 2007, pp. 126 430, vol. 318.
Kim et al., "Porous chitosan-based adhesive patch filled with poly(L-3,4-dihydroxyphenylalanine) as a transdermal drug-delivery system," Journal of Porous Materials, Feb. 2013, pp. 177-182.
J. Xie et al., "Controlled biomineralization of electrospun poly(E-caprolactone) fibers for enhancing their mechanical properties," Acta Biomatrialia, Mar. 2013, pp. 5698-5707, vol. 9.
G.R. Mitchell et al., "Role of Anisotropy in Tissue Engineering," Procedia Engineering, Jan. 2013, pp. 117-125, vol. 59.
M. Kim et al., "Polydopamine-Decorated Sticky, Water-Friendly, Biodegradable Polycaprolactone Cell Carriers," Macromol. Biosci., May 2016, pp. 738-747, vol. 16.
I. Manavitehrani et al., "Biomedical Applications of Biodegradable Polyesters," Polymers, Jan. 2016.
N. V Shah et al., "Current State and Use of Biological Adhesives in Orthopedic Surgery," Orthopedics, Dec. 2013, pp. 945-956, vol. 36.
P. J. Ginty, Abstract—"The supercritical processing of mammalian cells for applications in tissue engineering," PhD thesis, University of Nottingham, Apr. 2006.
P. J. Ginty, et al. "Mammalian cell survival and processing in supercritical C02", Proceedings of the National Academy of Sciences, May 2006, pp. 7426-7431, vol. 103.
S. Curia et al., "High-pressure rheological analysis of CO2-induced melting point depression and viscosity reduction of poly(E-caprolactone)" Polymer, Jul. 2015, pp. 17-24, vol. 69.
T. Kokubo et al., "How useful is SBF in predicting in vivo bone bioactivity?", Bioma I Erials, May 2006, pp. 2907-2915, vol. 27.
W. Choi et al., "Polydopamine Inter-Fiber Networks: New Strategy for Producing Rigid, Sticky, 3D Fluffy Electrospun Fibrous Polycaprolactone Sponges," Macromol. Biosci., Jun. 2016, pp. 824-835.
Y. Liu et al., "Polydopamine and its derivative materials: Synthesis and promising applications in energy, environmental, and biomedical fields", Chem. Rev., May 2014, pp. 5057-5115, vol. 114.
Mathieu et al., "Architecture and properties of anisotropic polymer composite scaffolds for bone tissue engineering", Biomaterials, Feb. 2006, pp. 905-916, vol. 27.
Mabrouk et al., "Enhancement of the biomineralization and cellular adhesivity of polycaprolactone-based hollow porous microspheres via dopamine bio-activation for tissue engineering applications" Materials Letters, Dec. 2015, pp. 503-507, vol. 161.
Bong Hoon Kim et al., "Directed self-assembly of block copolymers for universal nanopatterning", Soft Matter, Jan. 2013, pp. 2780-2786, vol. 9.
D. Zhang et al., "Porous inorganic—organic shape memory polymers", Polymer, Jun. 2012, pp. 2935-2941, vol. 53.
Jung-Hye Eom et al., "Processing and properties of macroporous silicon carbide ceramics: A review", Journal of Asian Ceramic Societies, Sep. 2013, pp. 220-242, vol. 1.

* cited by examiner

INJECTABLE AND EXPANDABLE COMPOSITION, DEVICES, KITS, METHODS AND USES THEREOF

CROSS-REFERENCE TO RELATED APPLICATIONS

This application is a U.S. National Stage Application under 35 U.S.C. § 371 of International Patent Application No. PCT/IB2018/057985, filed Oct. 15, 2018, which claims priority to European Patent Application No. 18152785.4, filed Jan. 22, 2018 and Portugal Patent Application No. 110348, filed Oct. 13, 2017, the contents of which are each hereby incorporated by reference in their respective entireties.

TECHNICAL FIELD

The present disclosure relates to injectable and expandable compositions, devices, kits and methods for use in an approach for the in-situ foaming of polymers for bone or tissue defects, to fill and/or fuse a tissue defect.

BACKGROUND ART

The adhesive technologies currently available have been extensively reviewed in the literature. Two distinct groups can be identified, synthetic adhesives and biologically inspired materials [']. Among the synthetic adhesives are poly(methyl methacrylate) bone cement, which is the class of synthetic materials that has more extensively been used in bone fixing fractures; cyanoacrylates; polyurethanes; dentine and enamel, used in dental applications; calcium and phosphate bone cements and glass ionomer cements. Synthetic adhesives have high adhesion strength however they present crucial disadvantages such as poor biocompatibility and limited biodegradability.

On the other hand, biologically inspired materials raise less biocompatibility concerns and may overcome the ability of synthetic adhesives to adhere in a wet environment. Nonetheless, these are not able to provide the mechanical integrity required for bone tissue applications and are instead more suitable as soft tissue adhesives. Biologically inspired adhesives include fibrin glue, gelatin-resorcinol-formaldehyde glue, protein-aldehyde systems, mussel proteins and biomimetic castles and glues from different animal species.

These facts are disclosed in order to illustrate the technical problem addressed by the present disclosure.

General Description

The present disclosure relates to compositions, devices, kits and methods for use in an approach for the in-situ foaming of polymers for bone or tissue defects, namely filling and/or fusion.

The design of extrudable and expandable compositions for bone fusion is one of the most challenging fields in the intersection of polymer and biomedical engineering.

An aspect of the present disclosure relates to an injectable expandable composition for use in medicine, veterinary or cosmetic, comprising:
  a bio-polymer or co-polymer polyester particle filler;
  a polydopamine adhesive bound to said filler;
  a polyacrylate plasticizer bound to said polydopamine adhesive.

An aspect of the present disclosure relates to an injectable expandable composition for use in medicine, veterinary or cosmetic, comprising a polycaprolactone particle filler; a polydopamine adhesive bound to said filler; a polymethacrylic acid plasticizer bound to said polydopamine adhesive, for treating a bone defect, in particular for treating a bone defect, for bone regeneration or for bone tissue engineering.

The injectable expandable composition of the present disclosure has surprisingly improved bioactive and adhesive properties suitable for treating a bone defect, for bone regeneration or for bone tissue engineering, namely for use in diverse trauma and pathology-driven needs in bone surgery.

In an embodiment for better results, the bio-polymer or co-polymer polyester particle filler may be selected from a list consisting of: poly (L-lactic acid), poly (D-L-lactic acid) (PLA); polyglycolic acid [Polyglycoside (PGA)], poly (glycol-co-trimethylene carbonate) (PGA/PTMC), poly (D, L-lactic-co-caprolactone) (PLA/PCL), poly (glycol-co-caprolactone) (PGA/PCL); polyethylene oxide (PEO), polydioxanone (PDS), polypropylene fumarate, poly (ethyl glutamate-co-glutamic acid), poly (tert-butyloxycarbonylmethyl glutamate), poly (carbonate ester), polycaprolactone (PCL), polycaprolactone co-butylacrylate, polyhydroxyalkanoate as polyhydroxybutyrate (PHBT), polyhydroxybutyrate copolymers with hydroxyvalerate (PHB/HV), poly (phosphazene), poly (phosphate ester), poly (amino acid) and poly (hydroxybutyrate), polydepsipeptides, copolymers of maleic anhydride, polyphosphazenes, polyiminocarbonates, cyanoacrylate, or mixtures thereof. Preferably, the filler may be a polycaprolactone, a polycaprolactone derivate, or mixtures thereof.

In an embodiment for better results, the polyacrylate plasticizer is selected from a list consisting of:
  poly(acrylates), poly(hydroxyalkylacrylates), poly(methacrylates), poly(hydroxyalkyl methacrylates), poly(alkyl acrylates), poly(alkyl methacrylates), poly(allyl methacrylates), poly(diacrylates), poly(triacrylates), poly(dimethacrylates), poly(trimethacrylates), poly(alkyl diacrylates), poly(glycerol methacrylates), poly (aminoalkyl acrylates), poly(aminoalkylmethacrylates), poly(aminoalkyldiacrylates), poly(aminoalkyl dimethacrylates), poly(ethoxybiphenol-A dimethacrylates), poly(ethyleneglycol methacrylates), poly(ethyleneglycol dimethacrylates), poly(ethyleneglycol trimethacrylates), poly(siloxanyl acrylates), poly(siloxanylmethacrylates), poly(siloxanyl alkyl acrylates), poly(siloxanyl alkyl methacrylates), poly(siloxanyl alkyl diacrylates), poly(siloxanyl alkyl dimethacrylates), poly(sylil methylene methacrylates). Preferably, polymethacrylic acid.

In an embodiment for better results, injectable expandable composition of the present disclosure may comprise 70-89.5 w % (w/w$_{composition}$) of a particle filler of bio-polymer or co-polymer, preferably 75-85 w % (w/w$_{composition}$) of a particle filler of bio-polymer or co-polymer; in particular polycaprolactone.

In an embodiment for better results, injectable expandable composition of the present disclosure may comprise 0.5-5% (w/w$_{composition}$) of polydopamine adhesive, preferably 1-4% (w/w$_{composition}$) polydopamine adhesive.

In an embodiment for better results, injectable expandable composition of the present disclosure may comprise 10-30% (w/w$_{composition}$) of polyacrylate plasticizer, preferably 15-25% (w/w$_{composition}$) of polyacrylate plasticizer, in particular polymethacrylic acid.

In an embodiment for better results, the particles of polycaprolactone have a size from 900-100 μm, preferably from 750-200 μm, more preferably from 600-300 μm.

In an embodiment for better results, injectable expandable composition of the present disclosure may further comprise: a bone growth stimulant, a bone growth promoter, a growth hormone, a cell attractant, a drug molecule, cells, bioactive glass, bioceramics—including: tricalcium phosphate, hydroxyapatite, calcium phosphate, calcium sulfate, calcium carbonate, aluminium oxide; or combinations thereof. These components may be added to the injectable expandable composition (before extrusion) and/or expanded foam material (after extrusion).

In an embodiment for better results, the drug molecule may be an anti-inflammatory, antipyretic, analgesic, anti-cancer, or mixtures thereof; in particular dexamethasone.

In an embodiment for better results, the bone growth promoter may be selected from: fibroblast growth factor, transforming growth factor beta, insulin growth factor, platelet-derived growth factor, oxysterols or mixtures thereof; in particular bone morphogenetic protein.

In an embodiment for better results, cells may be selected from: osteoblasts, osteoclasts, osteocytes, pericytes, endothelial cells, endothelial progenitor cells, bone progenitor cells, hematopoietic progenitor cells, hematopoietic stem cells, neural progenitor cells, neural stem cells, mesenchymal stromal/stem cells, induced pluripotent stem cells, embryonic stem cells, perivascular stem cells, amniotic fluid stem cells, amniotic membrane stem cells, umbilical cord stem cells, genetically engineered cells, bone marrow aspirate, stromal vascular fraction, or combinations thereof. These components may be added to the injectable expandable composition (before extrusion) and/or expanded foam material (after extrusion).

In an embodiment for better results, cells may be mammal cells. These components may be added to the injectable expandable composition (before extrusion) and/or expanded foam material (after extrusion).

The cells can be processing in supercritical $CO_2$ and survive. (P. J. Ginty. et. al, Mammalian cell survival and processing in supercritical $CO_2$, 2006, in Proceedings of the National Academy of Sciences, vol. 103, no. 19, page. 7426-31.)

In an embodiment for better results, injectable expandable composition of the present disclosure is an implantable composition.

In an embodiment for better results, injectable expandable composition of the present disclosure is an extrudable composition.

In an embodiment for better results, injectable expandable composition of the present disclosure for treating a bone defect, for bone regeneration or for bone tissue engineering, in particular bone fusion.

In an embodiment for better results, injectable expandable composition of the present disclosure for filling and fixing bone or tissue.

In an embodiment for better results, injectable expandable composition of the present disclosure for use in the treatment of bone defect resulting from pathologies including: post-traumatic pathologies, deformities, degenerative pathologies, infections, post-surgical or genetic pathologies, idiopathic or combinations thereof.

In an embodiment for better results, injectable expandable composition of the present disclosure for treating, inhibiting or reversing vertebral column diseases or disorders of intervertebral disc.

In an embodiment for better results, injectable expandable composition of the present disclosure in a method for prevention or treatment trauma and/or orthopaedic surgery comprising polycaprolactone, polydopamine and polymethacrylic acid,
    wherein said composition is administrated as a biodegradable material,
    wherein said material comprises particles of polycaprolactone, bound to polydopamine and
    wherein said polydopamine is bound to polymethacrylic acid.

Another aspect of the present disclosure relates to an expanded foam material for use in medicine obtainable by the method described in the present disclosure or comprising the injectable expandable composition of the present disclosure, comprising a porosity of 30-90%, preferably 40-60%.

In an embodiment for better results, the expanded foam material of the present disclosure comprises a pore size between of 100-900 µm, preferably 150-200 µm.

In an embodiment for better results, the expanded foam material of the present disclosure comprises a porous interconnectivity of 20-90%, preferably 25-70%, more preferably 30-50%.

In an embodiment, the morphological structure and the calculation of the morphometric parameters (Porosity (%), Interconnectivity (%), Mean pore size (mm), Density (mm-1) and degree of anisotropy) that characterize the 3D extruded foams can be calculated by micro-computed tomography (micro-CT) using a Skyscan 1272 equipment (Bruker, Germany) with penetrative X-rays of 50 KeV and 200 µA, in high-resolution mode with a pixel size of 21.6 µm. A CT analyser (v1.15.4.0, 2012-2015, Bruker Micro-CT) was used to calculate the parameters from the 2D images of the matrices.

Another aspect of the present disclosure relates to a spinal implant comprising the expanded foam material of the present disclosure can be obtained from the injectable expandable composition of the present disclosure.

Another aspect of the present disclosure relates to a method for obtaining an expanded foam material of the present disclosure, comprising the steps of:
    loading the injectable expandable composition described in any of the previous claims in a high-pressure chamber;
    sealing said high pressure chamber;
    pressurizing said high pressure chamber at 20-150 bar, preferably at 45-120 bar, more preferably at 50-60 bar.

In an embodiment for better results, the pressurizing step is carried in the presence of a pressurizing agent.

In an embodiment for better results, the pressurizing agent is selected from a list consisting of: nitrogen, nitrous oxide, ethanol, methanol, sulfur hexafluoride, cyclohexane, methane, toluene, p-xylene, tetrafluoromethane, perfluoroethane, tetrafluoroethylene, 1,1-difluoroethylene, carbon dioxide or mixtures thereof; preferably carbon dioxide.

In an embodiment for better results, the method further comprises a step of heating the high-pressure chamber to 35-90° C., preferably at 60° C., for 5-60 min, preferably for 15 min.

Another aspect of the present disclosure relates to a portable syringe for obtaining an expanded foam material of the present disclosure comprising a high-pressure chamber for the injectable expandable composition of the present disclosure;
    a pressurizing agent container;
    an inlet for the pressurizing agent into the pressure chamber;
    an outlet for the expanded foam material of the present disclosure;

heating system to heat the pressure chamber at a temperature of 35-90° C., preferably at 60° C., wherein the high-pressure chamber is able to work at a pressure between 20-150 bar, preferably 45-120 bar, more preferably 45-50 bar.

A kit comprising the injectable expandable composition of the present disclosure and the portable syringe for obtaining an expanded foam material of the present disclosure.

Table 1 establishes a comparison between synthetic and biologically inspired adhesives.

|  | Synthetic adhesives | Biologically inspired | PCL pDA pMAA |
|---|---|---|---|
| High level of adhesion in wet environment | + | ++ | + |
| Mechanical stability | + | − | ++ |
| Easy application (RT conditions) | + | NA | − |
| Adequate working time | ++ | ++ | + |
| Rapid setting time (1-10 min) | ++ | NA | + |
| Low exothermic reactions | − | ++ | ++ |
| Non-toxic and biocompatible | − | ++ | ++ |
| Allow healing of fracture | − | NA | ++ |

Table 1 presents the features required for bone adhesive materials and technologies to serve its purpose, wherein+ represents a good level of the feature; ++ represents a very good level of the feature; −represents a negative level of the feature; and NA, no available information in the literature.

From Table 1 it is clear that the best material should be in the intersection of a synthetic adhesive and a biomimetic approach. This was the rational for the development of a new bone adhesive material described in the present disclosure: a polycaprolactone based adhesive modified with polydopamine and polymethacrylic acid (PCL pDA pMAA).

Polycaprolactone (PCL) is a biocompatible, bioresorbable polymer, FDA approved for several applications in the human body, and widely studied for the preparation of bone implants. The ease of processing of polycaprolactone (PCL), given by its soluble nature in organic solvents, low melting point and glass transition temperature, make it very attractive for processing either by solvent-based technologies, in particular wet-spinning or electrospinning; or melt-based technologies, in particular extrusion, gas foaming or 3D printing.

Polycaprolactone (PCL) is an inert material, which, while being an advantage by conferring it biocompatible properties is also a disadvantage in the sense that the polymer is not bioactive per se. One way to overcome this is to functionalize the polymer. For example, the enhancement of the poor bioadhesive properties of polycaprolactone can be done by coating PCL with polydopamine (pDA).

Polydopamine (pDA) is a molecule inspired in the composition of mussel adhesive properties. Its ability to self-polymerize provide a versatile and easy way to functionalize and coat a large variety of materials, from metals to ceramics and polymers.[4,5] Different studies report the functionalization of polycaprolactone substrates for biomedical applications. Kim et al. report the decoration of polycaprolactone microspheres with pDA for cell therapy approaches[6]. In another work, the same group reports the design of inter-fiber networks of electrospun polycaprolactone fibers with pDA with enhanced mechanical and adhesive properties[7]. Not only dopamine enhances the adhesive properties of the material but also may induce bioactivity of the structures. Particularly it has been reported that coating PCL with poydopamine may induce the mineralization of the structure and the formation of a bone-like hydroxyapatite layer, promoting bone-bone bonding[8-10]. Hence, this approach represents major advantages to overcome the lack of biomineralization of pure PCL matrices.

On the other hand, polymethacrylic acid (pMAA), belongs to the acrylate family of synthetic adhesives. Despite their excellent adhesive properties, the use of these materials has been hindered particularly due to their toxicity. Nonetheless, the possibility to control the its concentration in a polymeric blend may overcome biocompatibility issues, while still enhancing the adhesiveness of the matrices, as demonstrated by Kim et al [¹].

In this present disclosure it was evaluated, not only the possibility to design a new bone adhesive but also the ability to create a bioactive and adhesive porous foam structure, which can be directly delivered into the site of lesion. In an embodiment, the composition described in the present subject-matter, namely the polycaprolactone-based polymeric material surprisingly confer adequate morphological, mechanical and biological properties to the implants. Rheological properties were tuned to allow the extrusion of the material from a dedicated surgical tool for in situ foaming, using subcritical carbon dioxide as porogen, designed specifically for this application.

BRIEF DESCRIPTION OF THE DRAWINGS

The following figures provide preferred embodiments for illustrating the description and should not be seen as limiting the scope of disclosure.

DETAILED DESCRIPTION

Figure 1:
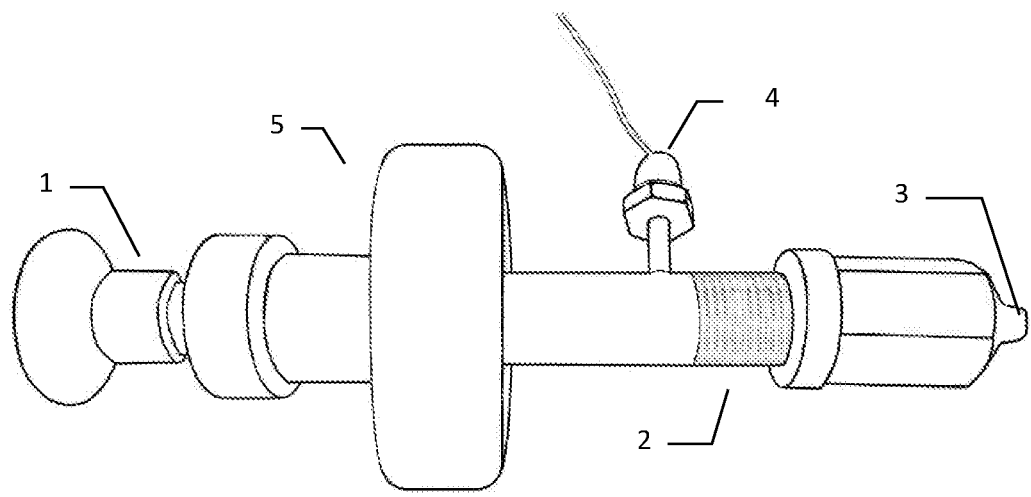
FIG. 1: Represents an embodiment of the device of the present disclosure wherein;
(1) represents the mechanical piston;
(2) represents the high-pressure chamber;
(3) represents the extrusion tip;
(4) represents the pressurizing agent inlet, namely $CO_2$;
(5) represents the handle;
(6) represents the sealing top.

The present disclosure relates to compositions, devices, kits and methods for use in an approach for the in situ foaming of polymers for bone tissue defect filling/fusion.

An aspect of the present disclosure relates to an injectable expandable composition for use in medicine, veterinary or cosmetic, comprising a polycaprolactone particle filler; a polydopamine adhesive bound to said filler; a polymethacrylic acid plasticizer bound to said polydopamine adhesive.

In an embodiment, the polycaprolactone doping with dopamine was carried out as follows. Polydopamine was grafted on the surface of PCL microparticles following the reported procedure by Kim et al[6] and Choi et al[7]. Briefly, PCL beads (Polycaprolactone average Mn 45.000, Sigma) were milled to powder using an Ultra centrifugal mill (Retsch ZM200) under liquid nitrogen. A solution of $10 \times 10^{-3}$ M Tris-HCl (TRIZMA® hydrochloride, CAS 1185-53-1, Sigma) was prepared and the pH adjusted to 8.5, using a sodium hydroxide (CAS 1310-73-2, Fisher Chemical, UK) solution (1 M). Dopamine-hydrochloride (CAS 62-31-7, Sigma) was added to the solution (2 mg·mL$^{-1}$) as well as the PCL microparticles and the solution was stirred overnight. The change in colour to dark brown indicates that the polymerization took place. The particles were recovered by filtration and were dialysed for three days in order to eliminate any residual monomer that did not react. The final samples of PCL-pDA were recovered and dried by freeze-drying.

In an embodiment, the polycaprolactone doped with dopamine and further grafted with polymethacrylic acid (pMAA) was performed as follows. Grafting polymethacrylic acid (pMAA) to PCL pDA samples was carried out in a subsequent step. In the formulation described in this disclosure, 20% wt/wt pMAA in respect to PCL pDA was tested. Based on the procedure reported by Kim and coworkers[11], 10 wt % of N-(3-Dimethylaminopropyl)-N'-ethylcarbodiimide polymer-bound (EDC) (EC-No 217-579-2) and N-Hydroxysuccinimide (NHS) (CAS 6066-82-6) were dissolved in poly(methacrylic acid, sodium salt) (pMAA) solution (CAS 79-41-4). The correspondent amount of PCL pDA was then added, together with 1 mL phosphate buffered solution (PBS) solution. The reaction was allowed to take place for 4 hours, after which the samples was precipitated with ethanol for 12 hours. The monomers which did not reacted were washed with ethanol and the sample was left to dry at room temperature.

In an embodiment, the characterization was performed by scanning electron microscopy (SEM), Fourier transform infrared spectroscopy (FTIR) and/or X-ray photoelectron spectroscopy (XPS).

In an embodiment, morphological properties of the samples prepared were analyzed by scanning electron microscopy (SEM) (JSM-6010 LV, JEOL, Japan). The samples were fixed by mutual conductive adhesive tape on aluminium stubs and were sputter-coated with gold before analysis.

In an embodiment, Fourier Transform Infrared Spectroscopy—FTIR analysis was used to evaluate the chemical modifications of PCL doped with pDA and pMAA. The samples were powdered and mixed with potassium bromide, and the mixture was moulded into a transparent pellet using a press (Pike). Spectra were recorded at 32 scans with a resolution of 2 cm$^{-1}$ (Shimadzu—IR Prestige 21).

In an embodiment, X-ray photoelectron spectroscopy (XPS) was used to evaluate the surface chemistry of the samples prepared to confirm the doping of PCL with dopamine. The chemical composition of 3 samples was examined by XPS surface measurements. The C 1s, O 1s, N 1s, Na 1s and survey spectra were recorded using a Kratos Axis-Supra instrument. Monochromatic X-ray source Al Kα (1486.6 eV) was used for all samples and experiments. The residual vacuum in the analysis chamber was maintained at around $8.5 \times 10{-9}$ torr. The samples were fixed to the sample holder with double sided carbon tape. Charge referencing was done by setting the binding energy of C 1s photo peak at 285.0 eV C1s hydrocarbon peak. An electron flood gun was employed to minimize surface charging i.e., charge compensation.

In an embodiment, the mechanical characterization was also carried out. Adhesion tests of the materials were performed in a first approach using a glass substrate, in particular a glass surface. All the adhesion experiments were conducted at room temperature. A contact area of 20×25 mm was employed. The material was melted, and the two plates were superimposed and maintained until solidification of the material. The bonded glass slides were placed on a universal testing machine with a load cell of 1 kN (INSTRON 5540, Instron Int. Lda, High Wycombe, UK)) in tensile mode and a crosshead speed of 2 mm·min$^{-1}$. The load was applied until detachment, which was confirmed by the graphic. The lap shear bonding strength was determined from the maximum of the force—deformation curve obtained. The results are presented as the average of at least three samples.

In an embodiment, the adhesion spinal plugs experiments were also performed: Ex vivo porcine spinal plugs (6×6×15 mm) were prepared from adjacent vertebrae. The intervertebral disc was removed, and vertebrae surfaces debrided by the aid of a surgical curette. Application of the PCL formulations in-between spinal plugs was performed as described for the glass surface testing experiments. The shear bond strength test was performed with a crosshead speed of 2 mm·min$^{-1}$ until complete fracture of the specimens. The maximum force (N) was recorded on a computer and divided by the bonded area (in mm$^2$) in order to calculate the bond strength (N/cm$^2$).

In an embodiment, the fractures were observed under a stereomicroscope (STEMI 1000, ZEISS) In an embodiment, cytotoxicity studies were conducted. An immortalized mouse lung fibroblasts cell line (L929), from European Collection of Cell Cultures, UK, was maintained in basal culture medium DMEM (Dulbecco's modified Eagle's medium; Sigma-Aldrich, Germany), plus 10% FBS (heat-inactivated fetal bovine serum, Biochrom AG, Germany) and 1% A/B (antibiotic-antimycotic solution, Gibco, UK). Cells were cultured in a humidified incubator at 37° C. in a 5% CO$_2$ atmosphere. The cytotoxicity evaluation was performed in accordance with ISO 10993-5:2009 guidelines. Confluent L929 cells were harvested and seeded in a 96 well plate (BD Biosciences, USA). Briefly, 100 μl of cell suspension with a concentration of $1 \times 10^4$ cells ml$^{-1}$ were added to the well. Cells were statically cultures for 24 hours in DMEM medium under the culture conditions previously described. The indirect contact was performed replacing the culture medium with the materials leachable. The leachables were obtained after 24 hours of extraction using a ratio 100 mg of material in 1 mL supplemented DMEM. A latex extract was used as positive control for cell death, and for negative control cell culture medium was used. The samples were cultured for 24 hours under a 5% $CO_2$ atmosphere at 37° C. and the cell viability was evaluated by the MTS assay. This assay is based on the bioreduction of a tetrazolium compound 3-(4,5-dimethylthiazol-2-yl)-5-(3-carboxymethoxyphenyl)-2-(4-sulphofenyl)-2H-tetrazolium) (Cell Titer 96® Aqueous Solution Cell Proliferation Assay, Promega, USA) into a water soluble brown formazan product. This was quantified by UV spectroscopy, reading the formazan absorbance at 490 nm in a microplate reader (Synergy HT, Bio-Tek Instruments, USA). The results are presented as a function of the absorbance for cells cultured in DMEM and correspond to the average of at least three measurements (±standard deviation).

In an embodiment, FIG. 1 represents the device developed to apply, by extrusion, the PCL pDA pMAA now disclosed comprising a mechanical piston (1), a high-pressure chamber (2), a extrusion tip (3) and a $CO_2$ inlet (4).

In an embodiment, the in-situ extrusion of modified PCL into bone defect (intervertebral disc space) was conducted as follows. Briefly, the extrusion is performed after loading the polymer (PCL pDA pMAA) in the high-pressure chamber, which is then sealed and pressurized with carbon dioxide at 50 bar (Air Liquide, 99.998 mol %). The device is heated up, in particular to 60° C., to promote the plasticization of the polymer and after, for example, 15 minutes of settling time, under these conditions it is possible to extrude the material through the tip of the device. The polymer is extruded in situ to the defect site and shaped to the defect geometry.

The defect site is performed in the intervertebral disc space. In an embodiment, the morphological structure and the calculation of the morphometric parameters that characterize the samples of PCL pDA pMAA were evaluated by micro-computed tomography (micro-CT) using a Skyscan 1272 equipment (Bruker, Germany) with penetrative X-rays of 50 KeV and 200 µA, in high-resolution mode with a pixel size of 21.6 µm. A CT analyser (v1.15.4.0, 2012-2015, Bruker Micro-CT) was used to calculate the parameters from the 2D images of the matrices.

In an embodiment, to evaluate the bioactivity of the samples of PCL pDA pMAA, these were soaked in 10 mL of simulated body fluid (SBF) solution during 1, 3, 7 and 14 days at 37° C. The SBF was prepared by dissolving NaCl, $NaHCO_3$, KCl, $K_2HPO_4.3H_2O$, $MgCl_2.6H_2O$ and $Na_2SO_4$ in distilled water and buffered with Tris (Hydroxymethyl) Aminomethane buffer and HCl to reach a pH value of 7.4, following the protocol described by Kokubo and Takadama [T. Kokubo, H. Takadama, How useful is SBF in predicting in vivo bone bioactivity? *Biomaterials* 2006, 27, 2907-2915.]. Tests were carried out in sterile conditions. Upon removal from SBF, the samples were rinsed with sterile distilled water and left to air dry before further analysis. PCL samples were used as negative control.

In an embodiment, scanning electron microscopy coupled with energy dispersive X-ray spectroscopy (SEM/EDS) was carried out as follows. The morphology and composition of the calcium-phosphates deposited on the surface of the matrices was investigated with a JSM-6010 LV, JEOL microscope with an integrated energy dispersive X-ray spectroscope (EDS) (INCAx-Act, PentaFET Precision, Oxford Instruments). To perform SEM, a conductive gold coating was applied to the samples. For EDS, the analyses were conducted at low vacuum and without any coating.

In an embodiment, X-ray diffraction (XRD) was used to evaluate the crystalline planes of the calcium-phosphates precipitated on the surface of the samples. The XRD diffraction patterns were collected on a Bruker D8 Discover, at a voltage of 40 kV and a current of 40 mA in a 2□ range from 10° to 60° with a step size of 0.02°.

Polycaprolactone (PCL) has been reported to be an excellent polymer for the development of scaffolds for tissue engineering, particularly for bone tissue engineering. Its properties, particularly its biocompatibility and degradation rate make it suitable for different applications in the field of regenerative medicine. However, this polymer per se does not present any bioactivity and it presents weak adhesive properties. Different strategies have been described in the literature to overcome these drawbacks. The triangular approach on tissue engineering of combining a polymeric scaffold with bioactive agents and cells is one way to overcome the fact that polymers are usually inert but have unequalled morphological and mechanical properties. In the present disclosure, a two-step approach for the modification of PCL was followed, providing it adhesive and bioactive properties.

Figure 2:
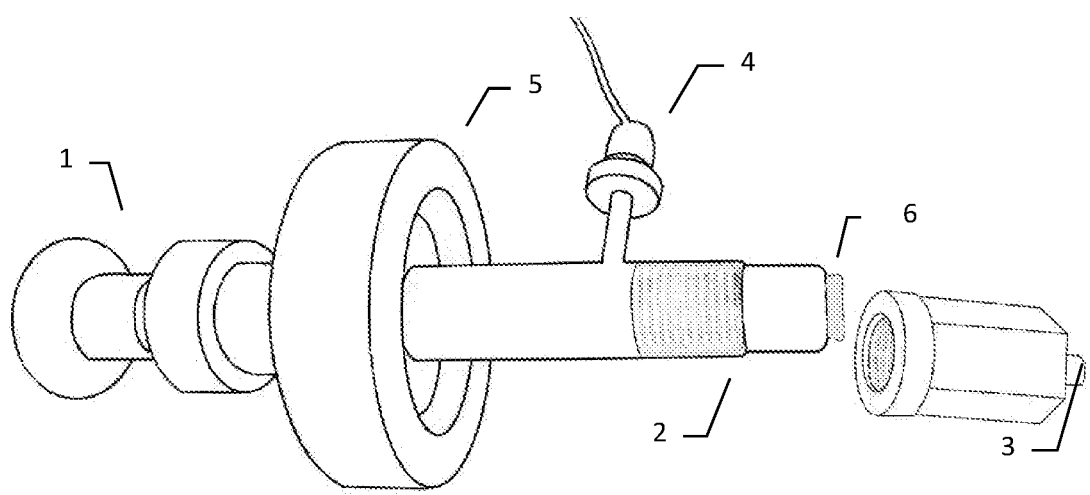
FIG. 2: Represents an embodiment of the device of the present disclosure with the high-pressure chamber open.

FIG. 2 represents the device wherein the high-pressure chamber (2) is unscrewed of the metal syringe structure (5) and the presence of both ends of the mechanical piston (1). This referred mechanical piston when pressed and closed creates an increased pressure in the high-pressure chamber (2) which forces the chemical compound leaving the chamber (2) by the extrude tip (3).

Figure 3:
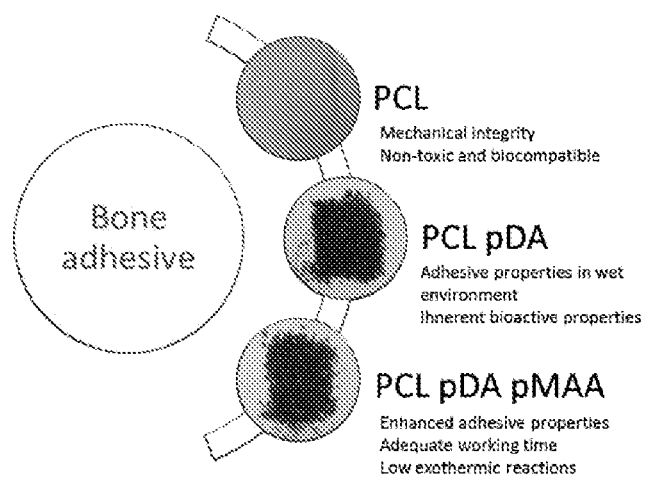
FIG. 3 schematically represents the chemical modification performed and the rational for the functionalization of the material with pDA and pMAA, and it also presents the characterization of the different samples, by SEM, FTIR and XPS.
Figure 3:
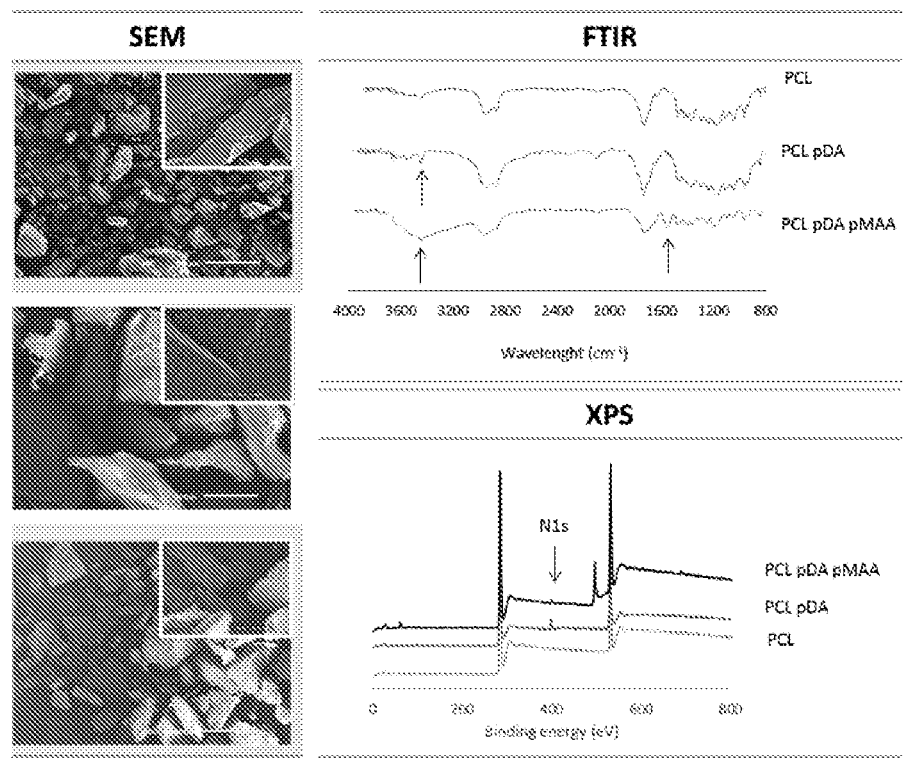

FIG. 3 schematically represents the chemical modification performed and the rational for the functionalization of the material with pDA and pMAA, and it also presents the characterization of the different samples, by SEM (scale bars 500 µm and 10 µm), FTIR and XPS.

In an embodiment, SEM images show all three types of samples, the pure PCL microparticles and the PCL microparticles modified with pDA and pDA+pMAA. At a higher magnification image, it is possible to see that addition of pDA results in a rougher surface, as compared to PCL. When adding pMAA this effect is even more noticeable. Chemical analysis of the polymers was carried out by FTIR and XPS. By FTIR it is possible to observe, as indicated by the arrows in the figure, the characteristic peak of the amine N—H stretching group in pDA at 3440 $cm^{-1}$. The presence of a single bands indicates that the secondary amine has reacted with PCL and a primary amine is present in the PCL pDA formulation. This is consistent with the information reported in the literature, namely on the description of the chemical reaction involved between dopamine and different substrates at pH 8.5 and Tris-solution[5,12]. When pMAA is grafted the amine group of dopamine may react with the carboxylic group of methacrylic acid and an amide is possibly formed. These observations are supported by the appearance of the characteristic bands of N—H bending of the amide II band at 1550-1510 $cm^{-1}$ and the N—H stretch at 3500-3400 $cm^{-1}$.

Figure 4:
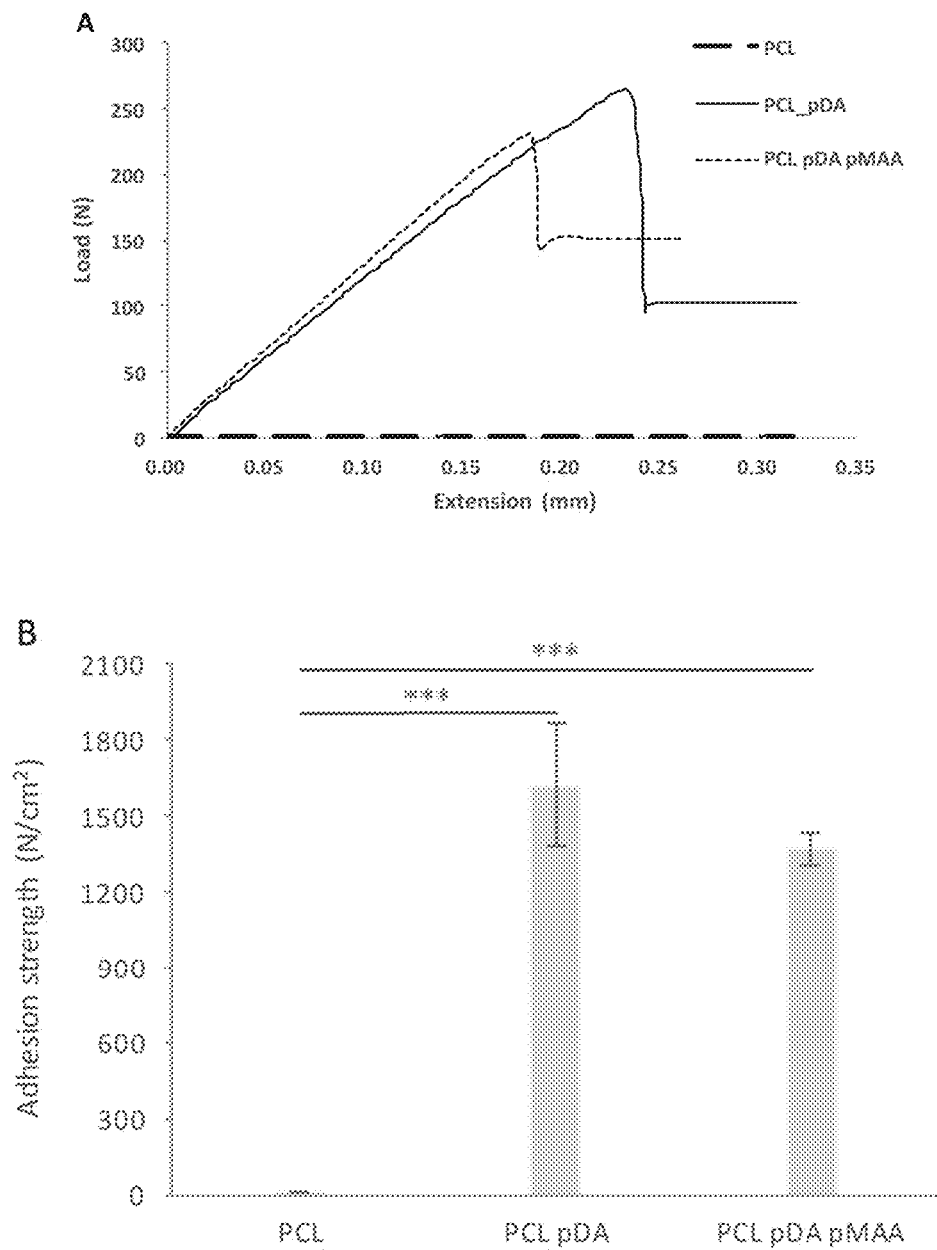
FIG. 4: Adhesion testing on glass surface (A) Force versus displacement curve for the different samples studied; (B) Adhesion strength for the different samples studied.

In an embodiment, the adhesive properties of the materials of the present subject-matter were characterized by mechanical testing. Two different studies were carried out in different conditions to evaluate the adhesion strength of PCL. In a first approach the adhesive properties were tested in a glass surface. Two glass plates were glued with the different materials and were subjected to a tensile force to evaluate the maximum load at detachment. FIG. 4A represents the load applied versus the extension and as can be observed, both PCL pDA and PCL pDA pMAA present similar behaviour and higher adhesive properties than PCL itself. Both pDA modified samples present maximum load before detachment between 200 and 300 N, whereas highest values were observed for the PCL pDA (265 N load).

In an embodiment, the adhesion strength can be determined from the maximum load taking into consideration the surface area. FIG. 4B presents the differences between the samples studied. PCL presents an adhesive strength of 0.074 (±0.02) $N/cm^2$, PCL pDA of 16.2 (±2.4) $N/cm^2$ and PCL pDA pMAA of 13.7 (±0.6) $N/cm^2$. In the embodiments, it was shown that modifying polycaprolactone with polydopamine and polydopamine plus methacrylic acid significantly enhances the mechanical properties of the polymer, particularly the adhesive properties of polycaprolactone ($p<0.001$). The differences in adhesion strength between PCL pDA and PCL pDA pMAA were, however not significantly different. The adhesive strength was further evaluated in spinal plugs, cut with a regular geometry. Adhesion with PCL, PCL pDA and PCL pDA pMAA was evaluated and the results are presented in FIG. 5.

Figure 6:
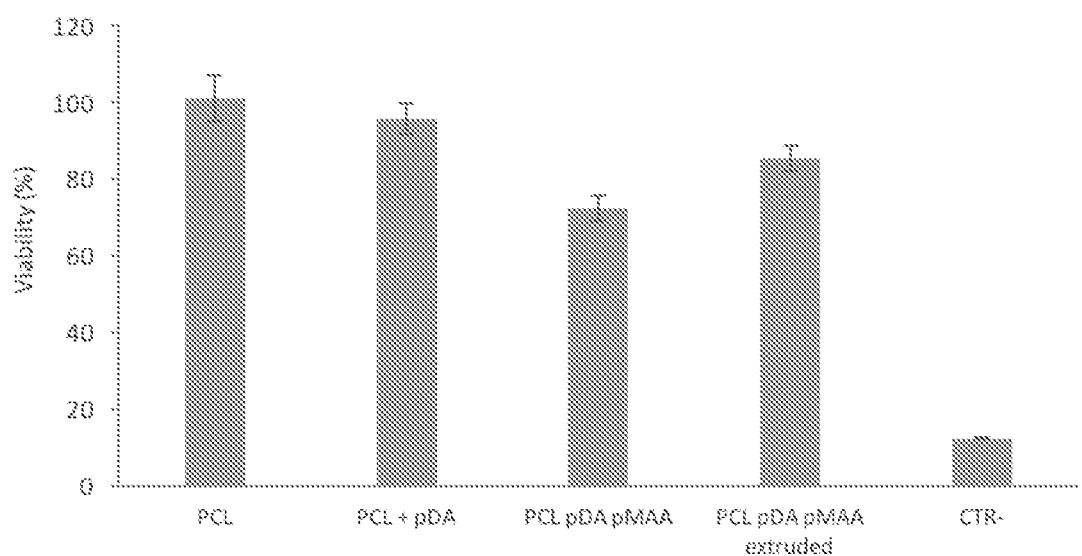
FIG. 6: Cell viability determined after the MTS assay

In an embodiment, cytotoxicity of the materials prepared was assessed by the MTS assay, according to the protocol described in the ISO 10993-5:2009. Extracts of the different formulations were tested and the viability was determined as a function of the negative control. FIG. 6 presents the results of cellular viability after 24 hours of cell culture in contact with the leachables of the materials, the cells may be added to the injectable expandable composition or to the expanded foam material after extrusion.

In an embodiment, the results demonstrate that the materials produced are non-cytotoxic once viability is above 70% in all groups. PCL pDA pMAA before and after extrusion presents distinct effect on cell viability (72% and 85%, respectively), whereas the final form of the biomaterial after extrusion presents a more favourable cellular response.

In an embodiment, the development of porous and interconnected structures from polycaprolactone has been explored through various different techniques. In the present disclosure, it was developed a portable high-pressure device (FIG. 1) for in situ polymer foaming based on the principles of gas foaming and extrusion. The use of supercritical carbon dioxide foaming for the preparation of porous structures for tissue engineering has been explored since 1996, when Mooney and coworkers proposed the use of $CO_2$ as a porogen agent for the preparation of poly-lactic acid foams [D. J. Mooney, D. F. Baldwin, N. P. Suh, J. P. Vacanti, R. Langer, Biomaterials 1996, 17, 1417]. The use of carbon dioxide as a porogen agent has significant advantages over others, namely the fact that this is a physical foaming agent. No chemical reaction takes place upon foaming, reducing the risk of production of any by-products that may be toxic. On the other hand, carbon dioxide foaming can be carried out under milder operating conditions due to the ability of carbon dioxide to act as a plasticizing agent and reduce the glass transition temperature and melting temperature of the polymer. Additionally, the polymer viscosity is also reduced improving the ease of manipulation and allowing an appropriate working time. Following the same principle, extrusion using carbon dioxide has become particularly interesting for the development of porous structures in a continuous mode, however, its potential has not been fully explored as large quantities of raw-materials are usually required in an extruder.

Figure 5:
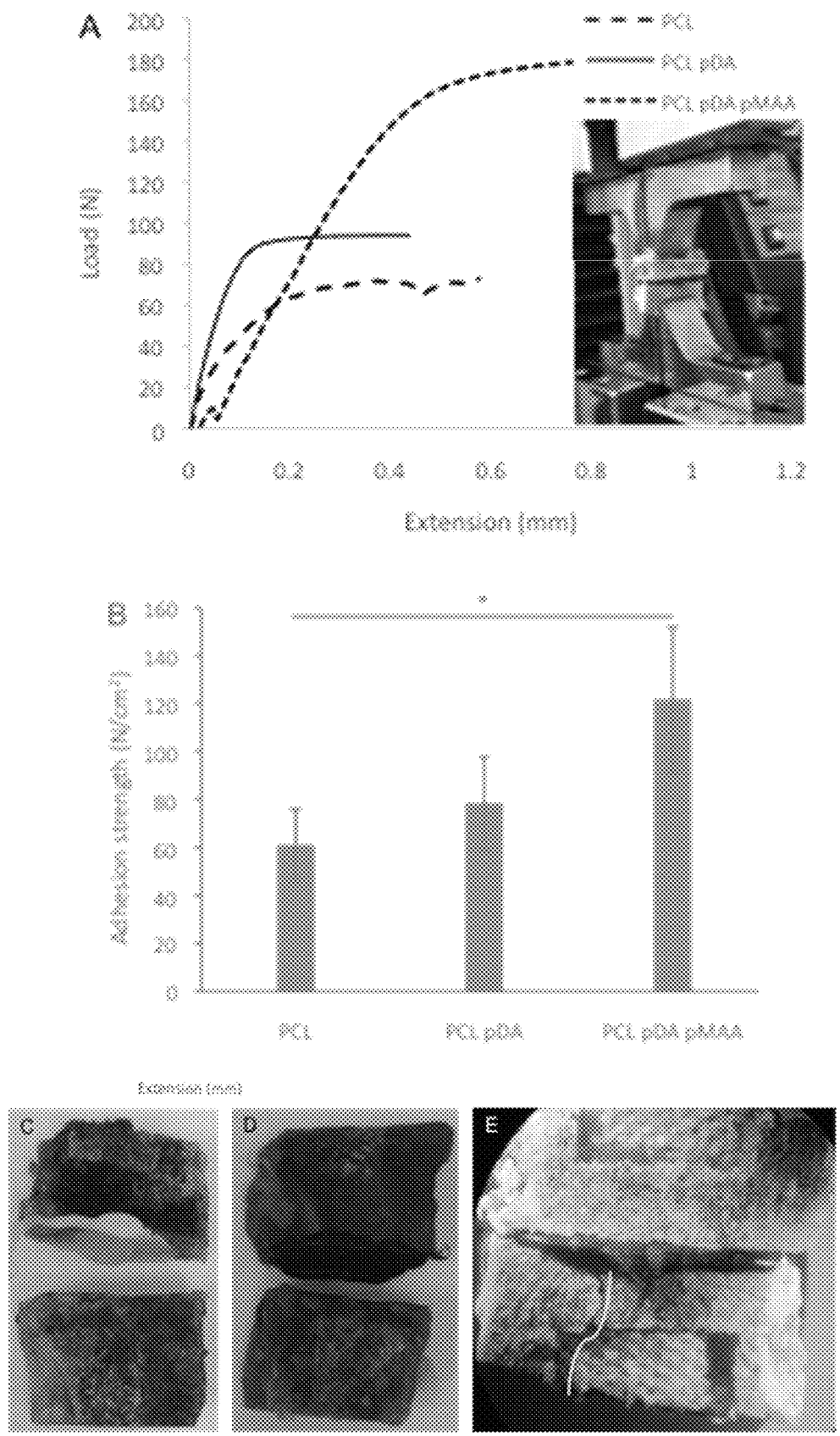
FIG. 5: Adhesion strength on spinal plugs (A) Force versus displacement curve and photograph of sample under testing; (B) Adhesion strength determined as a function of the material used; (C-E) macroscopic pictures of spinal plugs with different formulations after tensile testing: PCL, PCL pDA, PCL pDA pMAA respectively. Yellow line represents site of fracture.
Figure 7:
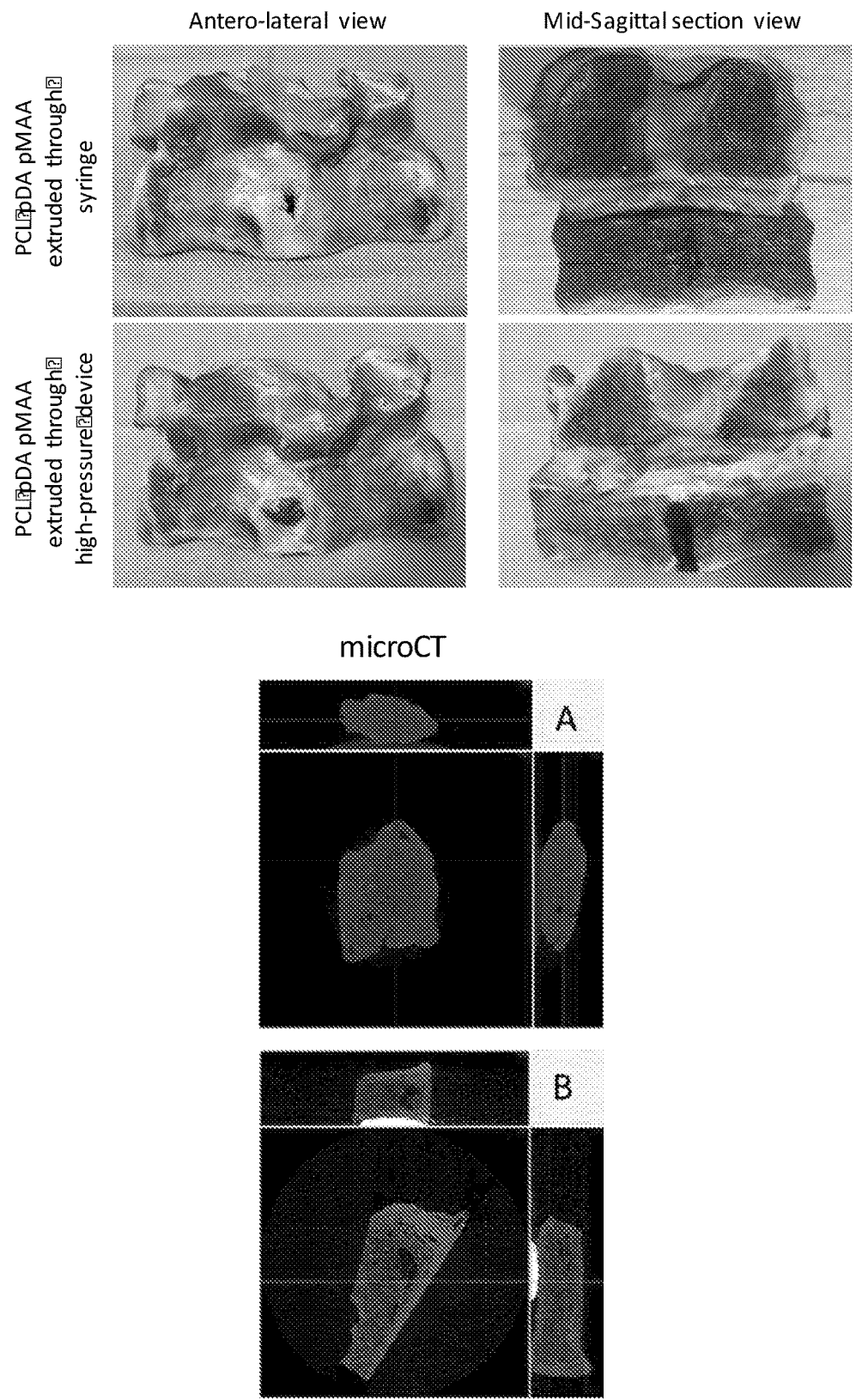
FIG. 7: Ex vivo testing of antero-lateral surgical technique in a porcine spine and micro computed tomography cross-section images (A and B) of the samples. Top row: PCL pDA pMAA extruded through a syringe; Bottom row: PCL pDA pMAA extruded through the high-pressure device into the intervertebral disk space.

Curia and co-workers have demonstrated the effect of carbon dioxide on melting temperature depression and the viscosity reduction of polycaprolactone under different operating conditions[13]. Their work shows that PCL (Mw 10,000) pressurized with 50 bar suffers a decrease in melting temperature of nearly 10° C. and a reduction in viscosity of nearly 50% comparing to its value at the same temperature at ambient pressure. In an embodiment, the preferred operating conditions are 60° C. and 50 bar. In order to mimic the antero-lateral surgical approach for lumbar interbody fusion, PCL pDA pMAA was extruded through the high-pressure portable device into the site of the defect, created in the intervertebral disc space of an ex vivo porcine spine, as shown in FIGS. 5 and 7. Hardening of the foam occurred within few seconds allowing immediate stabilization of the vertebrae. Such approach is deemed compatible for application to any other bone defects that require an adhesive filler and stabilization for regeneration. As control, the samples were also injected in the defect site through a syringe at ambient pressure. The solidified structures were taken from the defect site and the morphological parameters were analysed by micro-computed tomography. FIG. 7 presents the 3 axial cross-sections of both samples and as it can be observed the sample injected through the syringe is highly compact and presents residual porosity and interconnectivity. On the other hand, the sample extruded through the high-pressure device presents an interesting morphological profile, which is comparable to trabecular bone (Table 2).

TABLE 2

Morphological parameters of the samples extruded into the bone defect, determined by micro-CT at room temperature.

|  | PCL pDA pMAA extruded through syringe | PCL pDA pMAA extruded through high pressure device | Reference values for trabecular bone[14] |
|---|---|---|---|
| Porosity (%) | 3 | 45 | 52-96 |
| Interconnectivity (%) | — | 28 | — |
| Mean pore size (μm) | — | 169 | 450-1310 |
| Density ($mm^{-1}$) | 2 | 17 | 7-34 |
| Degree of anisotropy | 2 | 2.06 | 1.1-2.38 |

Figure 8:
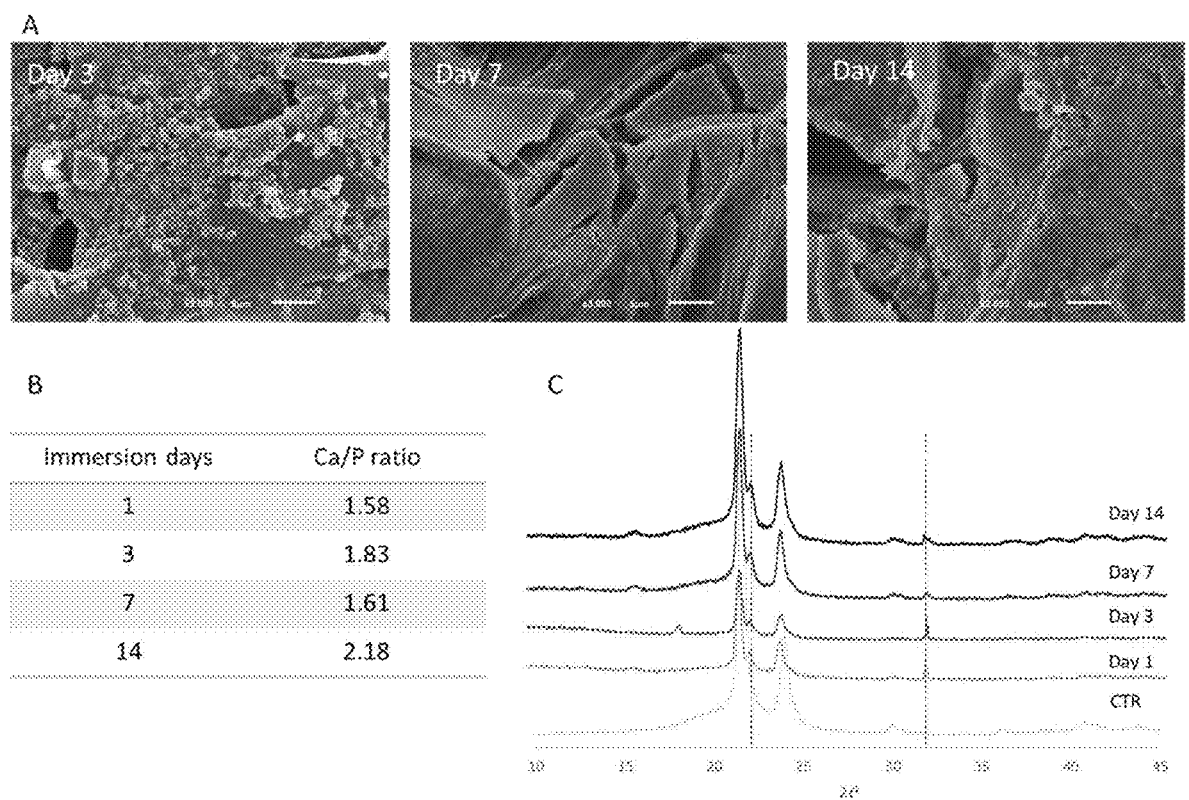
FIG. 8: Represents an embodiment of A) SEM images of PCL pDA pMAA immersed in SBF solution at different time points (scale bar: 5 □m); B) Ca/P atomic ratio calculated from the EDS data; C) XRD spectra of PCL pDA pMAA immersed at different time points, compared with PCL as control (CTR).

In an embodiment, the bioactivity or the ability of implants for bone regeneration to induce the formation of a bone-like hydroxyapatite layer has been reported to be a factor that strongly enhances the integration of the scaffold with the tissue, and therefore, the success of healing and tissue regeneration. The bioactive properties of PCL pDA pMAA were evaluated in a simulated body fluid, and as a control PCL samples were used. The samples were extruded through the device in the conditions described above (60° C. and 50 bar). FIG. 8 presents the SEM images of the materials after immersion as well as the chemical characterization of the calcium-phosphates precipitated on the surface.

Figure 9:
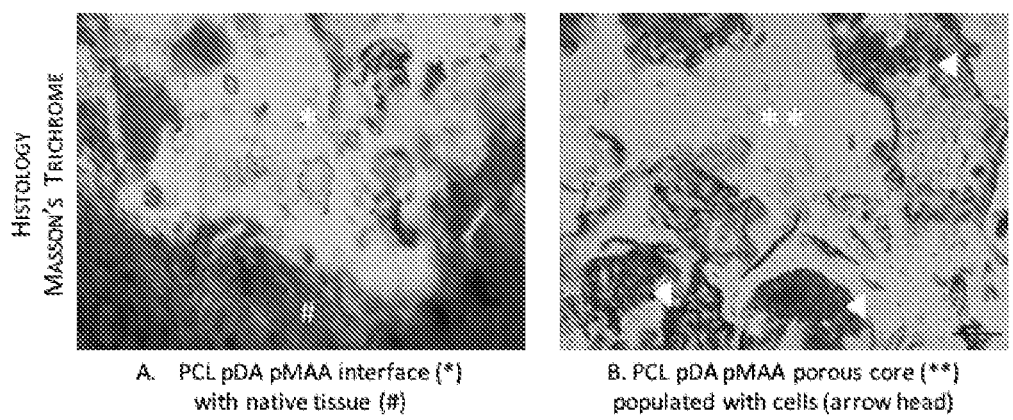
FIG. 9: In vivo evaluation of adhesion and bio-integration of the PCL pDA pMMA with native tissues: histological analysis (Masson's Trichrome).
Figure 10:
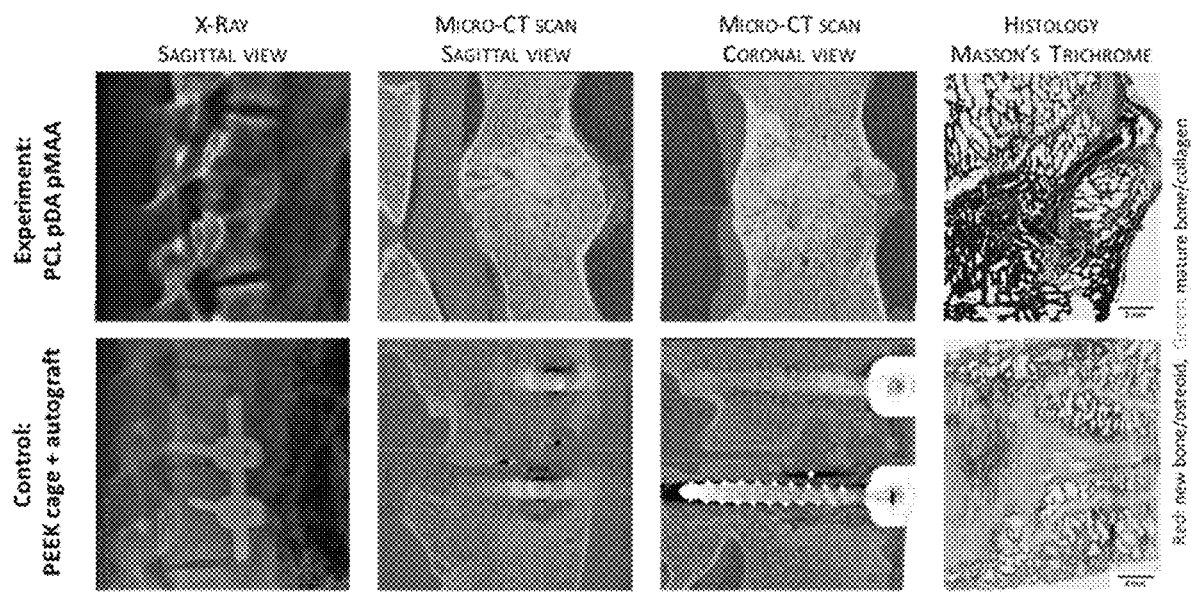
FIG. 10: In vivo spinal fusion performance assessment of PCL pDA pMMA as compared to PEEK cage+autograft (control) in a porcine model after 6 months: fusion was evaluated by radiological imaging (X-ray), micro-computed tomography (micro-CT) and histological analysis (Masson's Trichrome).

In an embodiment, the adhesive and bioactive properties of PCL pDA pMAA were assessed in a porcine spinal interbody fusion model for 6 months. The intervertebral disk was surgically removed and PCL pDA pMAA was extruded by the device to fill the void site. Immediate hardening of the material and adhesion to surrounding tissues occurred and no spinal instrumentation was used for stabilisation. FIG. 9A reveals integration of the PCL pDA pMAA with native tissues while FIG. 9B highlights the migration of surrounding cells to the porous core of the PCL pDA pMAA structure, becoming populated by cells to support new tissue formation. In vivo spinal fusion performance, as compared to PEEK cage+autograft (control), was further evaluated by radiological imaging (X-ray), micro-computed tomography (micro-CT) and histological analysis (Masson's Trichrome) (FIG. 10). Interbody fusion is seen in the intervertebral space treated by PCL pDA pMAA, evidenced by a continuous bone mass between upper and lower vertebral bodies which indicate osseous development within the previously void site.

A new PCL-based biopolymer was synthesized to achieve improved bioactive and adhesive properties aiming application as bone adhesive for diverse trauma and pathology-driven needs in bone surgery. Such biopolymer, composed of PCL pDA and pMAA was produced into a foam through a dedicated portable high-pressure device, towards direct application in bone defects. Such in situ foaming resulted in immediate stabilization of osseous components, while resulting in a 3D structure with morphological properties similar to those found in trabecular bone.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

Flow diagrams of particular embodiments of the presently disclosed methods are depicted in figures. The flow diagrams do not depict any particular means, rather the flow diagrams illustrate the functional information one of ordinary skill in the art requires to perform said methods required in accordance with the present disclosure.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

The following documents are herewith expressly incorporated by reference.

[1] D. F. Farrar, Bone adhesives for trauma surgery: A review of challenges and developments. *Int. J. Adhes. Adhes.* 2012, 33, 89-97.

[2] N. V Shah, R. Meislin, *Orthopedics* 2013, 36, 945.

[3] A. P. Duarte, J. F. Coelho, J. C. Bordado, M. T. Cidade, M. H. Gil, Surgical adhesives: Systematic review of the main types and development forecast. *Prog. Polym. Sci.* 2012, 37, 1031-1050.

[4] H. Lee, S. M. Dellatore, W. M. Miller, P. B. Messersmith, *Science* 2007, 318, 426.

[5] Y. Liu, K. Ai, L. Lu, Polydopamine and its derivative materials: Synthesis and promising applications in energy, environmental, and biomedical fields. *Chem. Rev.* 2014, 114, 5057-5115.

[6] M. Kim, J. S. Kim, H. Lee, J. H. Jang, *Macromol. Biosci.* 2016, 16, 738.

[7] W. Choi, S. Lee, S. H. Kim, J. H. Jang, *Macromol. Biosci.* 2016, 824.

[8] D. Zhang, O. J. George, K. M. Petersen, A. C. Jimenez-Vergara, M. S. Hahn, M. A. Grunlan, *Acta Biomater.* 2014, 10, 4597.

[9] J. Xie, S. Zhong, B. Ma, F. D. Shuler, C. T. Lim, *Acta Biomater.* 2013, 9, 5698.

[10] M. Mabrouk, D. Bijukumar, J. A. S. Mulla, D. R. Chejara, R. V. Badhe, Y. E. Choonara, P. Kumar, L. C. Du Toit, V. Pillay, *Mater. Lett.* 2015, 161, 503.

[11] J. H. Kim, J. I. Lim, H. K. Park, *J. Porous Mater.* 2013, 20, 177.

[12] B. H. Kim, D. H. Lee, J. Y. Kim, D. O. Shin, H. Y. Jeong, S. Hong, J. M. Yun, C. M. Koo, H. Lee, S. O. Kim, *Adv. Mater.* 2011, 23, 5618.

[13] S. Curia, D. S. A. De Focatiis, S. M. Howdle, *Polym. (United Kingdom)* 2015, 69, 17.

[14] L. M. Mathieu, T. L. Mueller, P. Bourban, D. P. Pioletti, R. Müller, J.-A. E. Månson, Biomaterials 2006, 27, 905.

[15] P. J. Ginty. et. al, Mammalian cell survival and processing in supercritical $CO_2$ 2006, in Proceedings of the National Academy of Sciences, vol. 103, no. 19, pag. 7426-31.

The invention claimed is:

1. An injectable expandable composition comprising:
   a polycaprolactone particle filler;
   a polydopamine adhesive bound to said polycaprolactone particle filler; and
   a polymethacrylic acid plasticizer bound to said polydopamine adhesive.

2. The injectable expandable composition of claim 1, wherein the composition comprises 70-89.5% (w/w$_{composition}$) of the polycaprolactone particle filler.

3. The injectable expandable composition of claim 2, wherein the composition comprises 75-85% (w/w$_{composition}$) of the polycaprolactone particle filler.

4. The injectable expandable composition of claim 1, wherein the composition comprises 0.5-5% (w/w$_{composition}$) of the polydopamine adhesive.

5. The injectable expandable composition of claim 4, wherein the composition comprises 1-4% (w/w$_{composition}$) of the polydopamine adhesive.

6. The injectable expandable composition of claim 1, wherein the composition comprises 10-30% (w/w$_{composition}$) of the polymethacrylic acid plasticizer.

7. The injectable expandable composition of claim 6, wherein the composition comprises 15-25% (w/w$_{composition}$) the polymethacrylic acid plasticizer.

8. The injectable expandable composition of claim 1, wherein the particles of polycaprolactone have a size from 100-900 μm.

9. The injectable expandable composition of claim 1, wherein the particles of polycaprolactone have a size from 200-750 μm.

10. The injectable expandable composition of claim 1, further comprising:
    a compound selected from the group consisting of: a bone growth promoter, a growth hormone, a cell attractant, a drug molecule, cells, bioactive glass, bioceramics, and combinations thereof,
    wherein the drug molecule is selected from the group consisting of: an anti-inflammatory, antibiotic, antipyretic, analgesic, anticancer, and mixtures thereof;
    wherein the bone growth promoter is selected from the group consisting of: fibroblast growth factor, transforming growth factor beta, insulin growth factor, platelet-derived growth factor, bone morphogenetic protein, oxysterols, and combinations thereof; and
    wherein the cells are selected from the group consisting of: osteoblasts, osteoclasts, osteocytes, pericytes, endothelial cells, endothelial progenitor cells, bone progenitor cells, hematopoietic progenitor cells, hematopoietic stem cells, neural progenitor cells, neural stem cells, mesenchymal stem cells, induced pluripotent stem cells, embryonic stem cells, perivascular stem cells, amniotic fluid stem cells, amniotic membrane stem cells, umbilical cord stem cells, genetically engineered cells, bone marrow aspirate, stromal vascular fraction, and combinations thereof.

11. The injectable expandable composition of claim 1, wherein the composition is an implantable composition and/or an extrudable composition.

12. An expanded foam material comprising the injectable expandable composition of claim 1.

13. The expanded foam material of claim 12, further comprising:
- a compound selected from the group consisting of: a bone growth promoter, a growth hormone, a cell attractant, a drug molecule, cells, bioactive glass, bioceramics, and combinations thereof,
- wherein the drug molecule is selected from the group consisting of: an anti-inflammatory, antibiotic, antipyretic, analgesic, anticancer, and mixtures thereof;
- wherein the bone growth promoter is selected from the group consisting of: fibroblast growth factor, transforming growth factor beta, insulin growth factor, platelet-derived growth factor, bone morphogenetic protein, oxysterols, and combinations thereof; and
- wherein the cells are selected from the group consisting of: osteoblasts, osteoclasts, osteocytes, pericytes, endothelial cells, endothelial progenitor cells, bone progenitor cells, hematopoietic progenitor cells, hematopoietic stem cells, neural progenitor cells, neural stem cells, mesenchymal stem cells, induced pluripotent stem cells, embryonic stem cells, perivascular stem cells, amniotic fluid stem cells, amniotic membrane stem cells, umbilical cord stem cells, genetically engineered cells, bone marrow aspirate, stromal vascular fraction, or combinations thereof.

14. A portable syringe for obtaining an expanded foam material of claim 12, comprising:
- a high-pressure chamber containing the composition of claim 1;
- a pressurizing agent chamber;
- an inlet for the pressurizing agent in the high-pressure chamber;
- an outlet for the expanded foam material; and
- a heating system to heat the high-pressure chamber at a temperature of 35-90° C.,
- wherein the high-pressure chamber operates at a pressure between 40-120 bar.

* * * * *